(12) United States Patent
Noda et al.

(10) Patent No.: US 8,334,144 B2
(45) Date of Patent: *Dec. 18, 2012

(54) APPARATUS FOR CHEMILUMINESCENT ASSAY AND DETECTION

(75) Inventors: Hideyuki Noda, Kokubunji (JP); Satoshi Ozawa, Musashino (JP); Masahiro Okanojo, Hachioji (JP); Kenko Uchida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,527

(22) Filed: May 23, 2012

(65) Prior Publication Data

US 2012/0231493 A1 Sep. 13, 2012

Related U.S. Application Data

(60) Continuation of application No. 12/976,031, filed on Dec. 22, 2010, now Pat. No. 8,197,751, which is a division of application No. 12/034,880, filed on Feb. 21, 2008, now Pat. No. 7,879,290.

(30) Foreign Application Priority Data

Apr. 20, 2007 (JP) ................................. 2007-112018

(51) Int. Cl.
G01N 21/76 (2006.01)
G01N 21/00 (2006.01)
G01N 21/75 (2006.01)

(52) U.S. Cl. ........ 436/172; 436/164; 422/52; 422/82.05
(58) Field of Classification Search .................. 436/172
See application file for complete search history.

(56) References Cited

U.S. PATENT DOCUMENTS

| 5,223,218 | A | 6/1993 | Fukuoka et al. | |
| 5,538,849 | A | 7/1996 | Uematsu et al. | |
| 5,637,874 | A | 6/1997 | Honzawa et al. | |
| 5,837,195 | A | 11/1998 | Malek et al. | |
| 7,879,290 | B2 * | 2/2011 | Noda et al. | 422/52 |
| 8,197,751 | B2 * | 6/2012 | Noda et al. | 422/52 |
| 2003/0148536 | A1 | 8/2003 | Liang et al. | |
| 2004/0022689 | A1 | 2/2004 | Wulf et al. | |
| 2006/0245976 | A1 | 11/2006 | Kawahito | |

FOREIGN PATENT DOCUMENTS

| JP | 03-010149 | 1/1991 |
| JP | 05-281143 | 10/1993 |
| JP | 7-83831 | 3/1995 |
| JP | 2000-314738 | 11/2000 |
| JP | 2002-153259 | 5/2002 |

OTHER PUBLICATIONS

Nippon Nōgeikagaku Kaishi vol. 78, No. 7, pp. 630-635, 2004. Office Action in Chinese Application No. 2008100058647 mailed Nov. 20, 2009.
Certified translation of JP 03010149.

* cited by examiner

Primary Examiner — Jill Warden
Assistant Examiner — Charles D Hammond
(74) Attorney, Agent, or Firm — Brundidge & Stanger, P.C.

(57) ABSTRACT

An apparatus includes a system for guiding chemiluminescence and a system for preventing a variation in dark currents. The apparatus includes a first light shielding BOX having a sample container holder and a shutter unit therein, the shutter unit including a top plate which is partly formed by a movement of a plate member, and a second light shielding BOX having a photodetector therein. While a measurement is not implemented, the shutter unit is closed to block entrance of stray light to the photodetector, and while a measurement is implemented, the plate member is moved to open the shutter unit, and the tip of the photodetector is inserted into a through hole formed in the top plate, so that the distance between the bottom of the sample container and a sensitive area of the photodetector is reduced to several millimeters or less.

8 Claims, 13 Drawing Sheets

US 8,334,144 B2

APPARATUS FOR CHEMILUMINESCENT ASSAY AND DETECTION

This application is a continuation application of U.S. application Ser. No. 12/976,031, filed Dec. 22, 2010, now U.S. Pat. No. 8,197,751, which is a divisional application of U.S. application Ser. No. 12/034,880 filed on Feb. 21, 2008, now U.S. Pat. No. 7,879,290. The entire dislcosures of which are incorporated herein by reference.

CLAIM OF PRIORITY

The present application claims priority from Japanese application JP 2007-112018 filed on Apr. 20, 2007, the content of which is hereby incorporated by reference into this application.

BACKGROUND OF THE INVENTION

1. Field of the Invention

The present invention relates to a chemiluminescence measuring apparatus for detecting chemiluminescence and bioluminescence of a substance which is contained in a liquid specimen, with high sensitivity and accuracy. The present invention also relates to a microbe count function for detecting ATP chemiluminescence of microbes to control a contamination level.

2. Background Art

Microbe monitoring for environmental control of medicinal chemical manufacturing plants and the like involves counting of airborne microorganisms, falling microorganisms, and adherent microorganisms. The method for counting is defined by International Organization for Standardization ISO 14698-1, and the cleanliness measured by the method is expressed by grades. Airborne microorganisms are generally measured by methods using the gravity-drop of airborne microorganisms or the airborne microorganism sampler which sucks a certain amount of air as disclosed in JP Patent Publication (Kokai) No. 2002-153259 A. In the methods, usually, microorganisms are collected on agar plates for a certain period of time to culture, and the cleanliness of the environment is evaluated by the number of colonies developed after the culture. The agar plates are generally cultured in a temperature controlled incubator for a few days, and the numbers of developed colonies are visually counted. The numbers of colonies in the agar plates are averaged to obtain the mean number of airborne microorganisms. In a manufacturing facility of aseptic medical products or Cell Processing Center (CPC) for producing cells which include clean rooms with a high level of cleanliness, among the above described grades, a grade A or B should be consistently maintained and controlled. These grades A and B correspond to the number of particulates in the air of 3,530/m$^3$ or less, and the number of microorganisms of 10 CFU (colony forming unit)/m$^3$ or less.

Meanwhile, for a contamination control of food, river, sewage disposal, and the like, a method is used in which luciferase and luciferin are added as chemiluminescence reagents to ATP (adenosine triphosphate) in microbes to measure the bioluminescence generated from the ATP. The obtained luminescence intensity is calculated into the number of microbes as disclosed in JP Patent Publication (Kokai) No. 2000-314738 A and JP Patent Publication (Kokai) No. 7-83831 A (1995) for example, so that the contamination level can be controlled. According to FIG. 6 of Nippon Nogeikagaku Kaishi Vol. 78, No. 7, pp. 630-635, 2004, the quantification limit of Escherichia coli is about 100 CFU/mL (with a reproducibility of 10.2% after N experiments where N=10). At the same time, according to FIG. 2 included in the instruction of a reagent kit which is shown in FIG. 6 of the above non-patent document, the quantification limit of Escherichia coli is about 200 CFU/mL, and the specimen solution supplied for measuring chemiluminescence is about 0.1 mL, which indicates that the quantification limit of Escherichia coli of this method is considered to be about 10 to 20 CFU.

ATP chemiluminescence assay can be applied to the measurement of airborne microorganisms. That is, microbes and dusts are collected onto an agar which is held in a Petri dish by an airborne microorganism sampler, and after an addition of a development solution, the number of airborne microorganisms included in the collected sample is calculated using ATP chemiluminescence, so that the number of living microbe, the microorganisms that are alive, is counted.

ATP chemiluminescence assay is conducted using a reagent kit provided by a certain manufacturer in accordance with the measurement procedure which is as follows:

(A) an ATP eliminating reagent is dispensed in a sample solution tube so as to eliminate killed microbes and ATP other than living microbes;

(B) another ATP eliminating reagent is dispensed in the sample solution tube so as to extract ATP from the living microbes;

(C) a chemiluminescence reagent is dispensed in the sample solution tube; and (D) move the tube which contains the chemiluminescence reagent and the mixed solutions to a black box of an apparatus for measuring the amount of chemiluminescence.

In such an ATP chemiluminescence assay, in order to measure ATP chemiluminescence with high sensitivity and accuracy, the use of a detector with high sensitivity and the achievement of a high concentration by an optical arrangement of the detector and a chemiluminescence reaction field are the important factors. Moreover, a light shielding set up for constraining the entrance of so-called stray light as much as possible is another important factor because the entrance of stray light which comes from the exterior of the apparatus or chemiluminescent substance into the apparatus decreases the accuracy of chemiluminescence measurement.

First, as to the detector with high sensitivity, conventionally, photomultipliers have been used as a photodetector of a microbe count apparatus which has a luminometer for ATP measurement or a luminometer using ATP chemiluminescence. When a higher sensitivity is needed, a single photon counting method (photon counting method) for digitally processing the signals from a photomultiplier is used.

Next, as to the optical arrangement, because a chemiluminescence intensity is decreased inversely by the distance square from a chemiluminescence emitting point, it is considered to be effective to place a specimen container having a chemiluminescence substance therein closer to a sensitive area. Also, the chemiluminescence from the luminous point is scattered in a sphere, the optical arrangement which allows an effective collection of the chemiluminescence to a sensitive are is important. A chemiluminescence collection efficiency is often defined using a solid angle, and according to the definition, a sensitive area which is closer to a container and larger relative to the luminous area is important to achieve a higher sensitivity. Also, specular members which surround a container holder are effective to cause chemiluminescence to be forcibly reflected at the specular surfaces to be introduced to the sensitive area.

Finally, to address stray light (to prevent an entrance of stray light), generally, a photodetector and a specimen container are covered with a light-shielding box, that is, the entire apparatus for chemiluminescent assay and detection is completely covered with a shielding body to block stray light.

However, a microbe count apparatus which uses ATP chemiluminescence has a solution control section therein for dispensing and collection of a solution in addition to a photodetector, which increases an area of the apparatus to be shielded, and also the material may includes a luminous element. This makes it difficult to block an entrance of stray light.

Thus, it is effective to partially shield an apparatus for chemiluminescent assay and detection from light, and JP Patent Publication (Kokai) No. 7-83831 A (1995) discloses a case where a luminometer is used to achieve the partial shielding. Generally, an openable/closable shutter unit is placed in front of a sensitive area of a photodetector to shield light (hereinafter, referred to as "double light shielding type"). The unit prevents an entrance of light to the chemiluminescence detecting means just prior to a sensitive area. Therefore, no stray light hits a light-receiving element, which prevents degradation and variation in dark currents due to an accumulation of lights caused by the stray light.

SUMMARY OF THE INVENTION

However, in the above described structure of the double light shielding type, when a light shielding set up is placed at the tip of a sensitive area, an openable/closable shutter unit is provided in front of the sensitive area. The shutter unit can be an obstacle which substantially increases the distance between a sample container and the sensitive area, and also increases the distance from a luminous point. This may cause a problem of a decreased sensitivity.

In addition, the conventional methods described above could not provided a sufficiently high sensitivity or measurement accuracy for detecting ATP chemiluminescence on the order of one microbe level which is required in manufacturing facilities of aseptic medical products and CPC, and so generally involves a pre-treatment process for culturing to increase microbes. This causes a problem that the processes become complicated and more than a half day is spent in the series of processes for obtaining the test result of cleanliness.

The present invention was made in view of the above situation, and the present invention provides an apparatus for chemiluminescent assay and detection with high sensitivity and accuracy which enables a simple operation for chemiluminescence measurement.

In order to solve the above described problems, an apparatus for chemiluminescent assay and detection according to the present invention includes: a container for storing a specimen; a holder for holding the container; a photodetector which is provided opposite to the container; a plate member which is provided opposite to the photodetector; a plate member driving section which causes the plate member to be moved relative to the photodetector; and a photodetector position control section which moves the photodetector relative to the container. The photodetector is provided opposite to the container via the plate member. The photodetector position control section moves the photodetector so that, when at least a part of the plate member is moved, an end surface of the photodetector is placed at the same position as that of a surface of the plate member which is opposite to the photodetector or at a position closer to the container than the opposite surface.

Also, an apparatus for chemiluminescent assay and detection according to the present invention includes: a container for storing a specimen; a holder for holding the container; a light-shielding housing having a top plate in which a through hole is formed so that the holder is placed over the through hole; a photodetector which is provided in the light-shielding housing in opposition to the bottom of the container via the top plate of the light-shielding housing; a photodetector position control section which moves the photodetector relative to the container; at least one nozzle; at least one solution reservoir; at least one piping tube; at least one feed pump which is connected to the piping tube; and a nozzle position control section which causes a nozzle to move into the container. The photodetector position control section controls the position of the photodetector so that an end surface of the photodetector is placed substantially at the same position as that of a surface of the top plate of the light-shielding housing opposite to the photodetector or at a position closer to the container than the opposite surface. The nozzle position control section controls the nozzle so that the nozzle is inserted into the container.

Moreover, an apparatus for chemiluminescent assay and detection according to the present invention further has a function to measure the amount of microbes. That is, the apparatus for chemiluminescent assay and detection includes: a first light-shielding housing having an open/close door; a container for storing a specimen; a holder for holding the container; a second light-shielding housing which is accessible through the open/close door, and has a top plate with a through hole formed therein so that the holder is placed over the through hole; a photodetector which is provided in the second light-shielding housing in opposition to the bottom of the container via the top plate of the second light-shielding housing; a photodetector position control section which moves the photodetector relative to the container; a dispensing means which has a nozzle, a solution reservoir, a feed pump, and a solution supply path; a fluid dispensing means which has a nozzle, a solution reservoir, a feed pump, and a solution supply path; and a nozzle position control section which causes a nozzle to move into the container. The apparatus for chemiluminescent assay and detection is provided with at least three dispensing means and at least one fluid dispensing means. The photodetector position control section controls the position of the photodetector so that an end surface of the photodetector is placed substantially at the same position as that of a surface of the top plate of the second light-shielding housing which is opposite to the photodetector or at a position closer to the container than the opposite surface. The nozzle position control section controls the nozzle so that the nozzle is inserted into the container. And then, an ATP-eliminating reagent, ATP extracting reagent, and a chemiluminescence solution by ATP-derived are introduced into each nozzle through the tip thereof so that the amount of microbes can be measured using a luminescence intensity of ATP in living microbes.

These and other features of the present invention will be apparent from the following description of the best embodiments to implement the present invention and the accompanying drawings.

According to the present invention, a double light shielding type box, specifically a second light-shielding box, prevents light accumulation due to stray light while chemiluminescence is not being measured, thereby a variation in background signals which depend on measurement accuracy is reduced, and while chemiluminescence is being measured, proximity effect induced by a photodetector and the bottom of a sample container enables a quantitative measurement of ATP of a very low concentration, thereby for example, a weak light emission of ATP chemiluminescence in one microbe can be measured with high sensitivity and accuracy, and microbes can be counted one by one.

DETAILED DESCRIPTION OF THE PREFERRED EMBODIMENTS

Figure 1A:
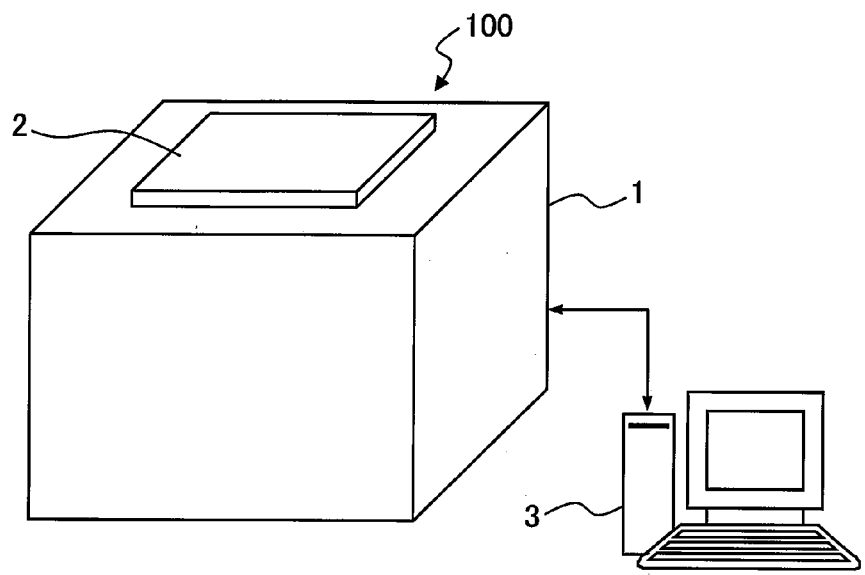
FIG. 1A is a view showing an outer structure of an apparatus for chemiluminescent assay and detection according to a first embodiment.

Now, embodiments of the present invention will be described below with reference to the accompanying drawings. However, it should be noted that the embodiments are illustrated only as examples to implement the present invention, and are not to be construed as limiting the present invention. The same reference numerals are given to the common elements throughout the drawings.

<First Embodiment>

Figure 1B:
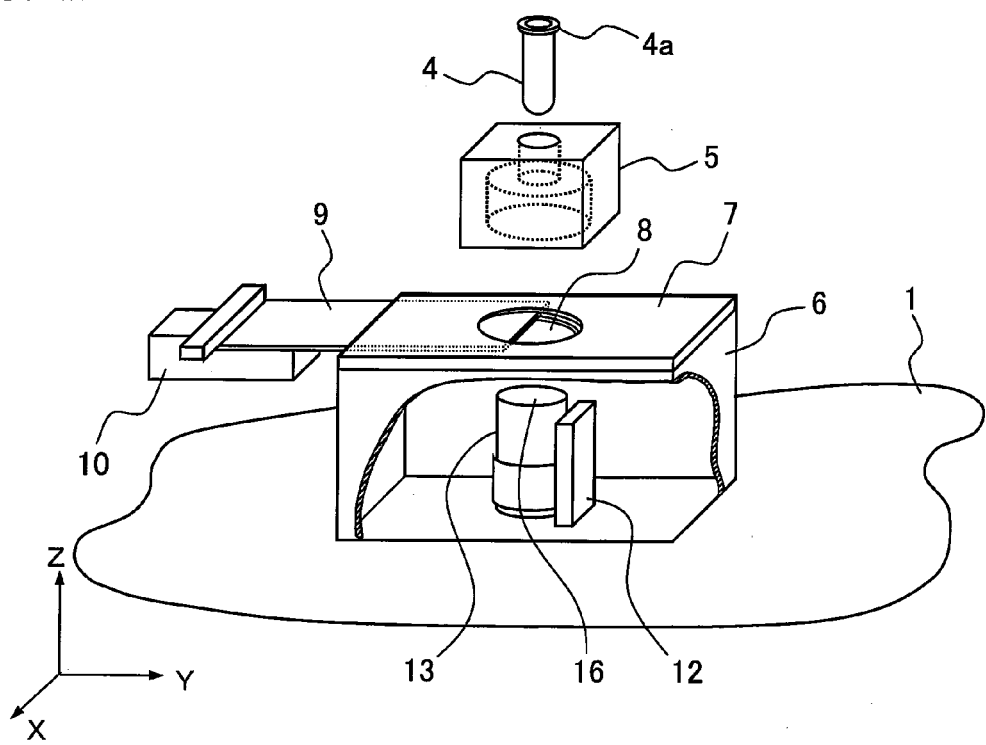
FIG. 1B is a view showing a schematic structure of the apparatus for chemiluminescent assay and detection according to the first embodiment.

FIG. 1 is a schematic view showing a structure of an apparatus for chemiluminescent assay and detection according to a first embodiment. FIG. 1A is an outline view showing a system which includes a chemiluminescence measuring apparatus 100 and a control device 3 for controlling the chemiluminescence measuring apparatus 100. The chemiluminescence measuring apparatus 100 includes a first light shielding BOX 1 and an open/close door 2 which is opened/closed to install a sample container. The inner structure of the chemiluminescence measuring apparatus 100 is shown in FIG. 1B. FIG. 1B is shown as an exploded view for simplicity of illustration.

A sample container 4 is installed in a sample container holder 5. The sample container holder 5 is placed over a through hole 8 which is formed in a top plate 7 of a second light shielding BOX 6. The sample container holder 5 is configured to be positioned on the top plate 7 when placed thereon. For example, a frame may be provided to the top plate 7 to place the sample container holder 5 at a fixed position, or a square groove may be formed in the top plate 7 to receive the bottom of the sample container holder 5 so that the sample container holder 5 can be fitted in the groove.

As shown in FIG. 1B, the sample container holder 5 is configured to have overlapped two cylinders of different diameters, and is through the top and bottom of the sample container holder 5. The structure of the sample container holder 5 will be explained in detail below by way of other examples. The sample container 4 is inserted through an opening of the upper cylinder of the smaller diameter, and is fixed using a flange 4a which is provided at the top of the container. Thus, the sample container 4 is mounted to the sample container holder 5 in a state of being hung from the holder 5. When a sample container 4 without a flange is used, an exclusive stopper or the like (not shown) provided to the sample container 4 may be prepared.

The top plate 7 of the second light shielding BOX 6 is formed so that the plate member 9 can be inserted therethrough, and the inserted plate member 9 is able to move in the direction of the y-axis through the top plate by a first actuator 10. The through hole 8 functions as an openable/closable window in accordance with the movement of the plate member 9.

The second light shielding BOX 6 has a photodetector 13 housed therein. The photodetector 13 is able to move in the direction of the z-axis using a second actuator 12. The sample container 4, the sample container holder 5, the center of the through hole 8, and the center of an entrance window 16 of the photodetector 13 are coaxially aligned in the direction of the z-axis. These elements are aligned when the apparatus is assembled. The first actuator 10 and the second actuator 12 may be those which are controlled by an electrical supply or an air supply.

The photodetector 13 is generally preferably a photomultiplier (Photomultiplier Tube: PMT) in terms of sensitivity. However, in a case where the required sensitivity is not so high as that of a PMT and a reduced cost of the apparatus is more important, a semiconductor device such as a photodiode may be used. However, only a system using a PMT will be described herein. In a PMT (photodetector 13), the parts except around the entrance window 16 is covered with a conductive shield, and in the present invention, the shield is grounded to the chemiluminescence measuring apparatus to prevent electrostatic charge on the photodetector 13.

FIG. 2 is a view illustrating the operation principle of the chemiluminescence measuring apparatus 100 of FIG. 1.

Figure 2A:
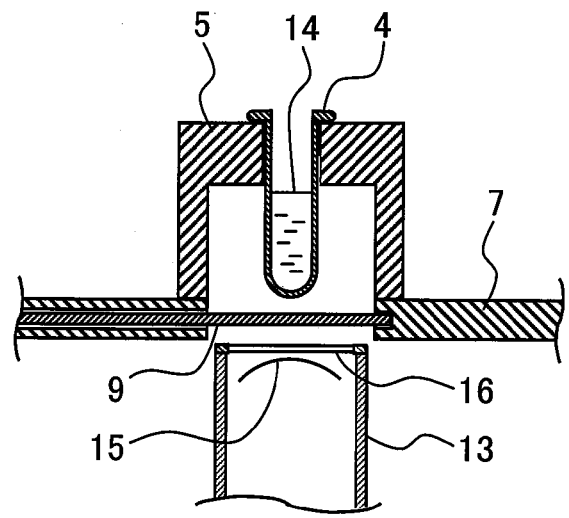
FIG. 2A is a view (1) showing the operation principle of the apparatus for chemiluminescent assay and detection according to the first embodiment.

FIG. 2A is a view showing a state just to start a measurement after the open/close door 2 is opened to insert the sample container 4 having a chemiluminescent material sample 14 therein in the sample container holder 5 and the open/close door 2 is closed. In the process for placing the sample container 4, the through hole 8 is closed by the plate member 9, thereby any stray light which may enter the inside of the second light shielding BOX 6 when the first light shielding BOX 1 is opened is completely blocked.

Figure 2B:
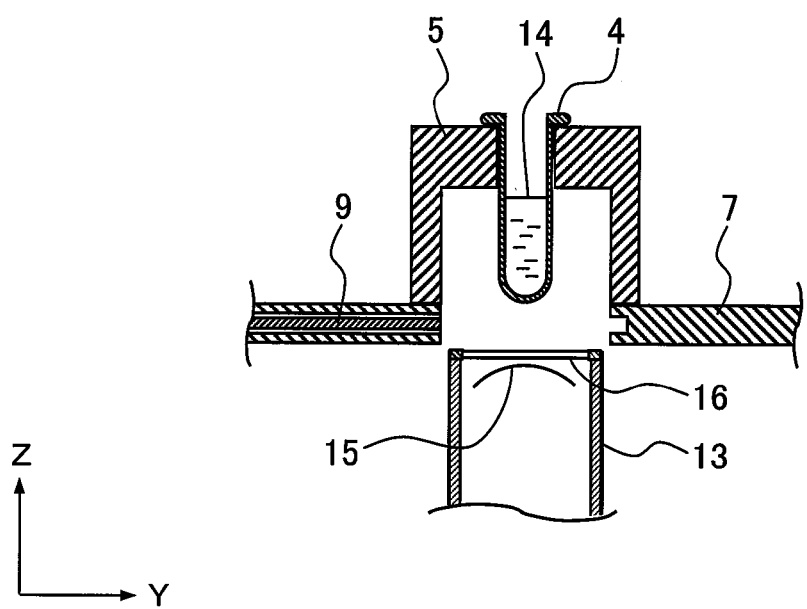
FIG. 2B is a view (2) showing the operation principle of the apparatus for chemiluminescent assay and detection according to the first embodiment.

A command from the control device 3 to start a measurement causes the plate member 9 to move in the direction of the y-axis, as shown in FIG. 2B. This displaces the bottom of the sample container 4 in a position opposite to a photocathode surface area 15 and the entrance window 16 of the photodetector 13.

Figure 2C:
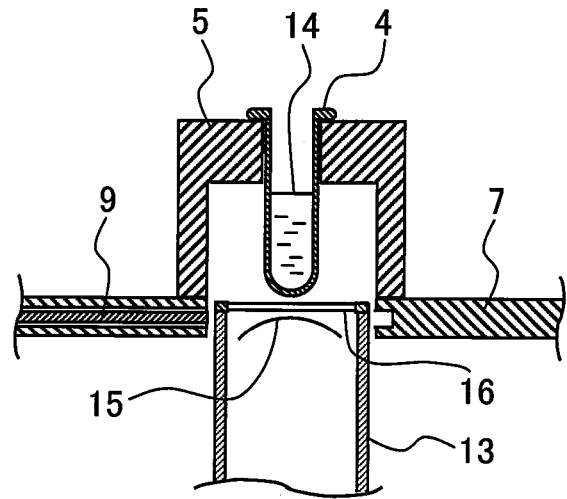
FIG. 2C is a view (3) showing the operation principle of the apparatus for chemiluminescent assay and detection according to the first embodiment.

Next, the second actuator 12 is driven to cause the photodetector 13 to get closer to the bottom of the container 4 (FIG. 2C). The entrance window 16 and a part of the photocathode surface area 15 at the tip of the photodetector 13 are inserted in the through hole 8 of the top plate 7 to a position closer to the bottom of the sample container 4 in the direction of the z-axis as compared to the distance between the bottom of the sample container 4 and the plate member 9.

In the state shown in FIG. 2C, a high voltage (HV) is applied to the photodetector 13 to start a chemiluminescence measurement.

Needless to say, since the second light shielding BOX 6 blocks stray light from the outside of the first light shielding BOX 1, the HV may be applied before the sample container 4 is placed in the sample container holder 5. However, for an extraordinary situation of the apparatus such as breakdown of a driving system of the plate member 9, the HV is preferably turned off while the open/close door 2 of the first light shielding BOX 1 is in an open state.

Figure 2D:
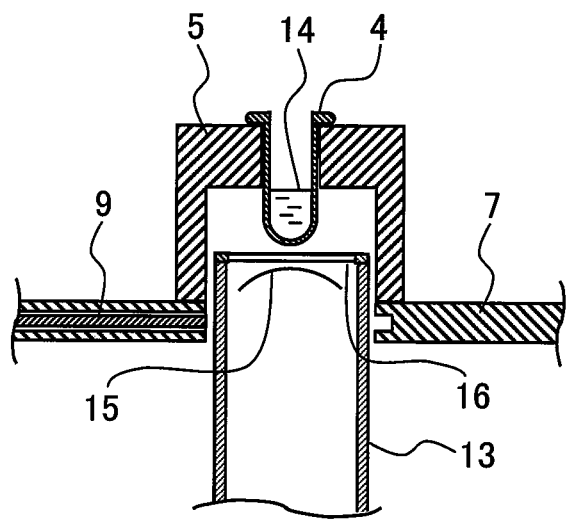
FIG. 2D is a view (4) showing the operation principle of the apparatus for chemiluminescent assay and detection according to the first embodiment.

FIG. 2D shows a case where another sample container 4 is used, the container 4 having a smaller volume and a shorter length in the direction of the z-axis than those of FIGS. 2A-2C. The photodetector 13 can be positioned using the second actuator 12 as needed, and also can be moved to a position above the plate member 9 in the direction of the z-axis, which keeps the distance from the luminous point, specifically the distance from the bottom of the sample container 4 and the photocathode surface area 15, to be constant even when the size of the sample container 4 is changed.

Alternatively, both of the sample container 4 and the sample container holder 5 may be moved to get closer to the photodetector 13. However, in this case, if the number of the sample to be measured is not one, that is, there is a plurality of sample containers 4 to be serially and automatically measured, actuators for each sample container 4 should be provided to individually control the distances between the sample containers 4 and the photodetector 13, which results in an increased size of the apparatus. Therefore, it is preferred to use the above described approach for moving the photodetector 13. In addition, the fact was found that, when a weak light emission like biochemiluminescence for a trace amount of ATP is measured, a simple operation to take out a sample container from a container holder and then insert the container to the same holder considerably influences the resulting measurements and may cause errors. The reason of the influence has not resolved in detail yet, but a slight change in the state of the electrostatic charge on a sample container may adversely affect the measurements. In spite of the reasons, the approach to move a sample container and its holder has a potential to cause the problem of error. While, when the sample container 4 is fixed to prevent any change in an electrostatic charge state and the photodetector 13 under static control is moved, similar to the above described approach to move the photodetector, the elimination of the potential can be effected.

The control of a distance between the sample container 4 and the photodetector 13 can be achieved by storing a moving distance parameter of the second actuator 12 for each type of the sample container 4 in a storing medium of the control device 3 in advance so as to read out the parameter as needed. The bottom of the sample container 4 must not contact the entrance window 16 of the photodetector 13. This is because a high voltage is applied to the photocathode surface area of the photodetector 13 and so the entrance window 16 is electrically charged to some degree. Also, since the sample container 4 is often made of plastic which is electrostatically charged, a simple access to the container 4 may cause an electrostatic discharge. The distance between the sample container 4 and the entrance window 16 is desirably set within a range from a several hundred micrometers to a several millimeters.

Figure 3A:
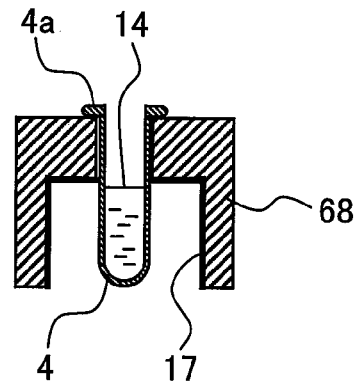
FIG. 3A is a view showing a structure (1) of a sample container holder which is used in the apparatus for chemiluminescent assay and detection according to the first embodiment.
Figure 3B:
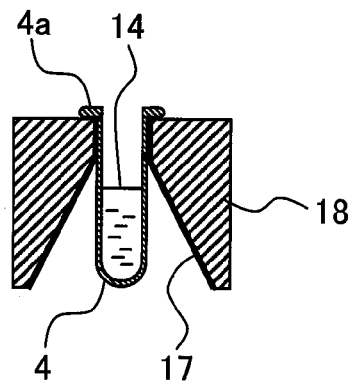
FIG. 3B is a view showing a structure (2) of a sample container holder which is used in the apparatus for chemiluminescent assay and detection according to the first embodiment.
Figure 3C:
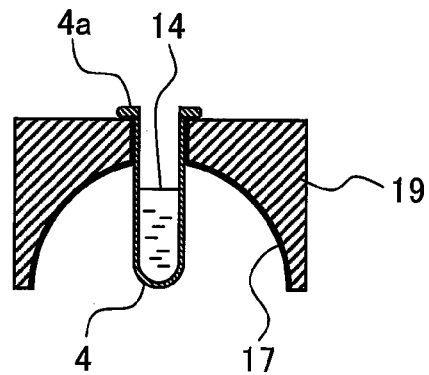
FIG. 3C is a view showing a structure (3) of a sample container holder which is used in the apparatus for chemiluminescent assay and detection according to the first embodiment.

An improved sensitivity can be expected when the sample container holder 5 efficiently guides the chemiluminescene in the sample container 4 to the entrance window 16. In order to collect the chemiluminescene which is scattered in the directions other than that toward the entrance window 16, specular reflection is often used. The container holder is preferably processed with a metal material, or the inner surface of the sample container holder 5 is formed with a member having a metal film 17 thereon, as shown in FIGS. 3A-C. It is advantageous, in terms of cost, to make a moldable resin material coated with a metal film. The metal material is preferably silver or aluminum which provides a stable reflection efficiency of 80% or more.

FIG. 3 shows typical three types of the sample container holder 5 having a metal film for specular reflection 17. A circular cylindrical sample container holder 68 is the form which allows the most efficient approach of the photodetector 13 relative to the size of the sample container 4, but provides a low collection efficiency of reflected chemiluminescence to the entrance window 16 of the photodetector 13. The reference numeral 18 designates a tapered sample container holder, and the reference numeral 19 designates a hemispherical sample container holder. These metal films enable the guiding of the chemiluminescene scattered from a luminous point to the entrance window 16 of the photodetector 13.

<Second Embodiment>

Figure 4:
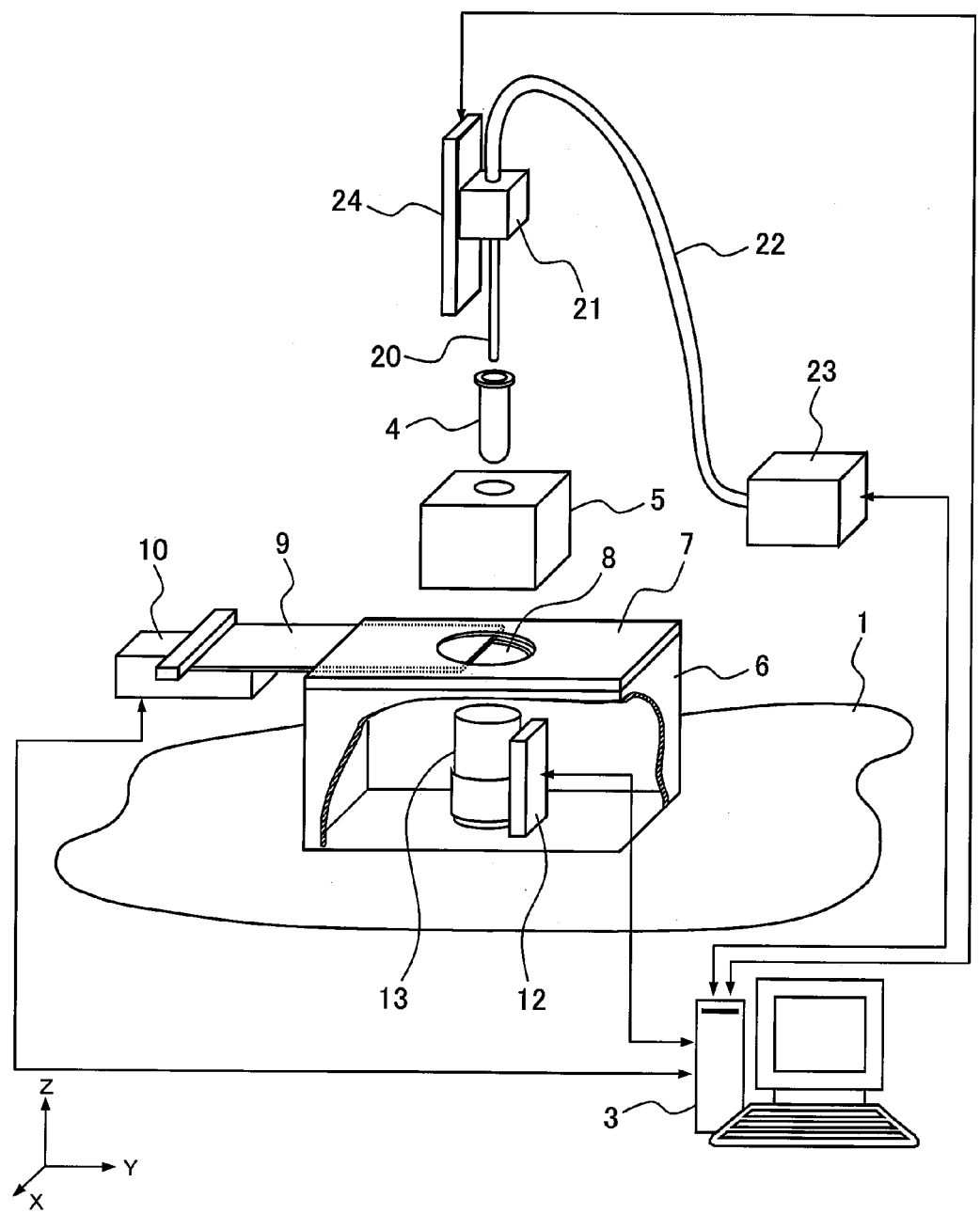
FIG. 4 is a view showing a schematic structure of an apparatus for chemiluminescent assay and detection having a dispenser according to a second embodiment.

FIG. 4 is a view showing a schematic structure of an apparatus for chemiluminescent assay and detection according to a second embodiment. The apparatus for chemiluminescent assay and detection of the present embodiment includes a solution dispenser in addition to the structure of the first embodiment (a chemiluminescence measuring apparatus having a dispenser).

In FIG. 4, a sample container 4 is mounted to a sample container holder 5. The sample container holder 5 is placed over a through hole 8 which is formed in a top plate 7 of a second light shielding BOX 6. The sample container holder 5 is aligned in the same manner as that of the first embodiment.

The top plate 7 of the second light shielding BOX 6 is configured to have a plate member 9 inserted therethrough. The inserted plate member 9 is able to move in the direction of the y-axis through the top plate 7 by the first actuator 10. The through hole 8 functions as an openable/closable window for introducing chemiluminescene by the movement of the plate member 9.

The second light shielding BOX 6 stores a photodetector 13 therein. The photodetector 13 is able to move in the direction of the z-axis by a second actuator 12.

The dispenser is configured with a dispensing nozzle 20 from which a solution exits when the solution is dispensed into the sample container, a feed pump 23, a liquid supply pipe 22 which connects between the dispensing nozzle 20 and the feed pump 23, and a piping connector 21 for fixing the dispensing nozzle 20 and connecting between the dispensing nozzle 20 and the liquid supply pipe 22. The position of the dispensing nozzle 20 is controlled in the direction of the z-axis by a third actuator 24. The third actuator 24 may be, for example, mounted to a gate-shaped plate member which is attached to the first light shielding BOX 6.

Preferably the sample container 4, the sample container holder 5, the through hole 8, the photodetector 13, and the dispensing nozzle 20 are coaxially aligned with each other at the center thereof in the direction of the z-axis.

FIG. 5 is a view showing the operation principle of the apparatus for chemiluminescent assay and detection according to the second embodiment (FIG. 4: a chemiluminescence measuring apparatus having a dispenser). FIG. 5 shows an example in which a chemiluminescence reagent, that is a substance or enzyme, and also substance+enzyme is added through the dispensing nozzle 20 into the sample container 4 so that the sample 25 in the sample container 4 having a chemiluminescent material emits luminescence. Of course, alternatively, another form may be used in which a chemiluminescence reagent may be stored in the sample container 4 in advance, and a sample to be measured may be supplied through the dispenser. When a trace amount of sample is measured, the latter form in which a sample is supplied through the dispenser is more preferable. Also, when a chemiluminescence reagent itself has some luminescence signals, the latter form in which a sample is supplied through the dispenser is more preferable.

Figure 5A:
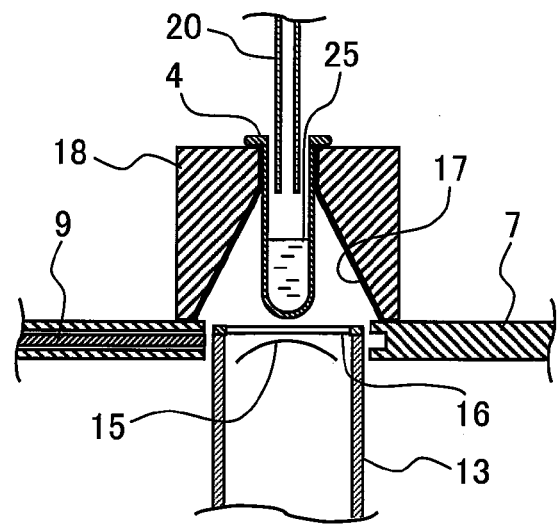
FIG. 5A is a view (1) showing the operation principle of the apparatus for chemiluminescent assay and detection having a dispenser according to the second embodiment.
Figure 5B:
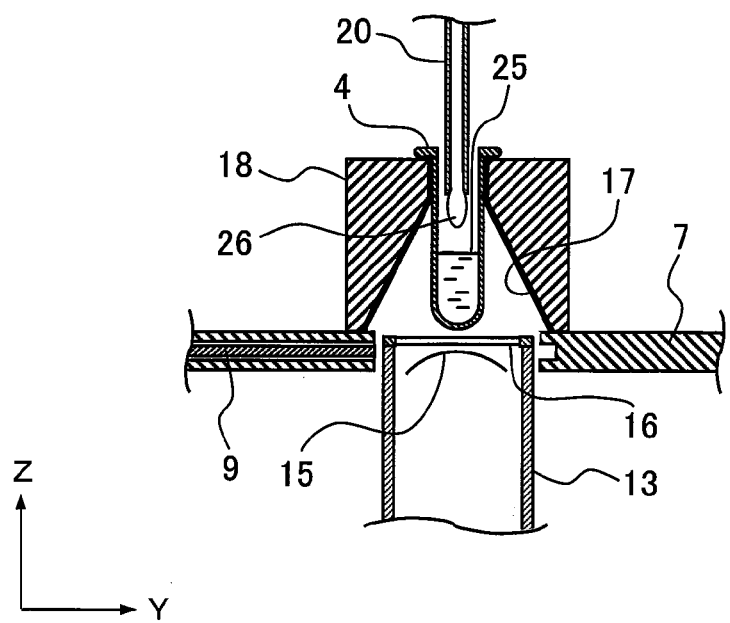
FIG. 5B is a view (2) showing the operation principle of the apparatus for chemiluminescent assay and detection having a dispenser according to the second embodiment.

FIG. 5A shows a state in which the plate member 9 moves in the direction of the y-axis, and the second actuator 12 is driven, and the photodetector 13 gets closer to the bottom of the sample container 4 in response to an instruction from the control device 3 to start a measurement. FIG. 5A further shows the moment when the dispensing nozzle 20 is inserted in the sample container 4. FIG. 5B shows the state that a chemiluminescence reagent is dispensed from the dispensing nozzle 20, and a dispensed droplet 26 is removed from the dispensing nozzle 20, while FIG. 5C shows the state that the dispensed droplet 26 is released into the sample 25 which contains a chemiluminescent material in the sample container 4 to form a luminescent solution 27.

Figure 5C:
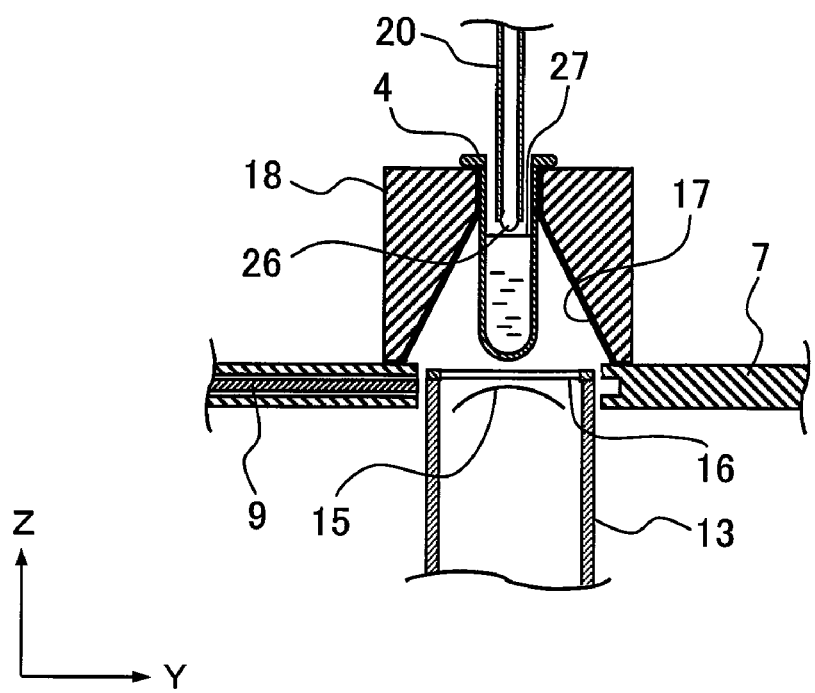
FIG. 5C is view (3) showing the operation principle of the apparatus for chemiluminescent assay and detection having a dispenser according to the second embodiment.

The application of an HV to the photodetector 13 may be conducted at any timing shown in FIGS. 5A-5C. Depending on the intention of a user, any timing to apply an HV can be set using the control device 3.

Next, an experiments to construct a calibration curve which shows the detection sensitivity and quantitativity of an ATP amount which is obtained using an apparatus for chemiluminescent assay and detection of the present embodiment, and the results of the experiment will be explained below. A luciferase & luciferin based chemiluminescence reagent was added to ATP to obtain chemiluminescent signals.

In advance, an ATP concentrated solution having a high concentration is diluted with a buffer such as deionized water and tris (hydroxymethyl) aminomethane solution, and the obtained ATP solution within a range from 1 amol to 100000 amol is stored in the sample container 4. A chemiluminescence reagent is stored in the feed pump 23 of the dispenser which has a solution reservoir. As an initialization operation of the apparatus, the second actuator 12 is driven to cause the photodetector 13 to be separated from the through hole 8, and the through hole 8 is closed by the plate member 9 to block any light entry to the inside of the second light shielding BOX 6 (to establish the state shown in FIG. 2A).

Figure 6:
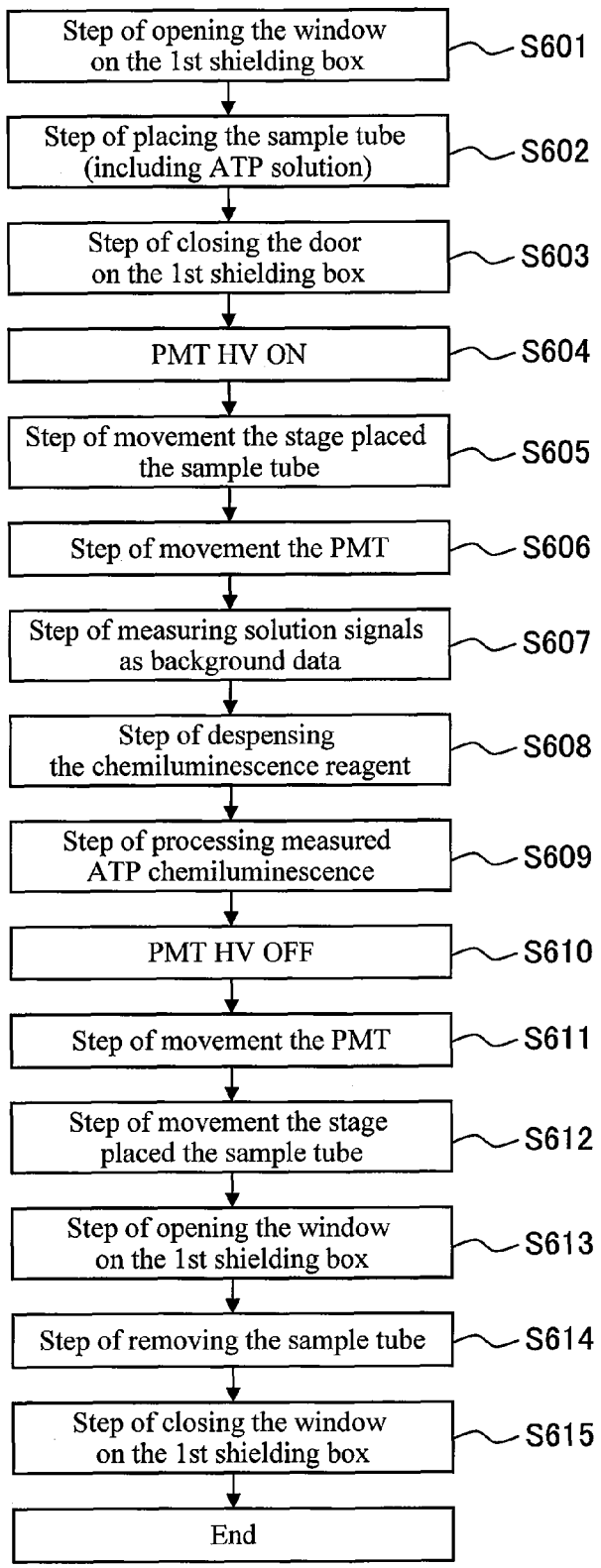
FIG. 6 is a flowchart illustrating a procedure for measuring ATP chemiluminescence using the apparatus for chemiluminescent assay and detection having a dispenser according to the second embodiment.

FIG. 6 is a flowchart illustrating a (typical) procedure for measuring chemiluminescence. First, the open/close door 2 of the first light shielding BOX 1 is opened (S601), and the sample container 4 having the ATP solution stored therein is placed in the BOX 1 (S602). Then, the open/close door 2 of the first light shielding BOX 1 is closed (S603). Next, an HV is applied to PMT which is the photodetector 13 (S604). The plate member 9 which is provided to the top plate 7 of the second light shielding BOX 6 moves (S605), and the PMT is moved by the second actuator 12 into the through hole 8 of the top plate 7 to get closer to the sample container 4 which is placed at a higher position in the direction of the z-axis than that of the plate member 9 (S606). After the movement of the optical system is completed, a measurement is started.

The measurement is started before a chemiluminescence reagent is dispensed from the dispenser 20, and the solution signals in the sample container 4 are measured as background data (S607). After the measurement of solution signals as background data for a certain period of time, the chemiluminescence reagent is dispensed from the dispenser 20 (S608). The chemiluminescence reagent reacts with the ATP in the sample container, and a chemiluminescent reaction is started in the container. After the measurement of ATP chemiluminescence for a certain period of time (S609), the HV to a PMT is turned off (S610), and the second actuator 12 is driven to move the tip portion of the photodetector 13 to a position below the plate member 9 in the direction of the z-axis (S611). After the movement of the PMT, the plate member 9 moves back to a position before the measurement, which closes the through hole 8 (S612). Next, in order to remove the sample container 4 after measurement, the open/close door 2 of the first light shielding BOX 1 is opened (S613), and the sample container 4 is removed (S614). To start measurement of a next sample, a container having the sample therein is placed at this step, and the above described flow for measurement is repeated. To end the measurement, after the sample container 4 is removed, the open/close door 2 of the first light shielding BOX 1 is closed to end the measurement (S615).

Desirably, among the steps shown in FIG. 6, those except the step of opening the first light shielding BOX (S601), the step of placing the sample container (S602), the step of closing the first light shielding BOX (S603), and the step of removing the sample container (S614) are automatically conducted, and a user only has to press a start button provided on the control device 3 for a serial execution of the steps. The waiting time for each step is not indicated herein, but may be changed and set as needed as a parameter which can be set using the control device 3.

Figure 7A:
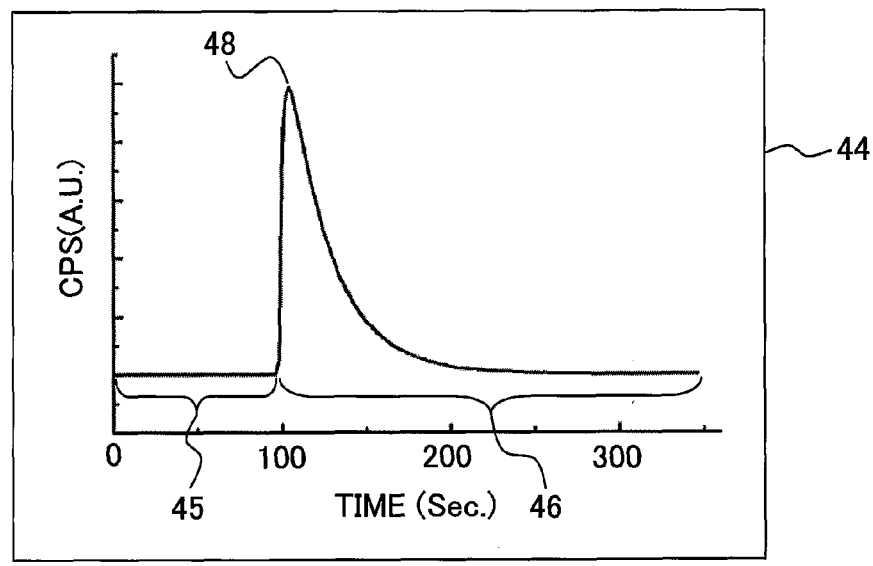
FIG. 7A is a graph showing an ATP chemiluminescence curve relative to time which is obtained using an apparatus for chemiluminescent assay and detection having a dispenser according to the second embodiment.

FIG. 7A is a graph showing a typical example of a chemiluminescence curve 44 relative to time which is obtained in the steps shown in FIG. 6 using the device shown in FIG. 5. The horizontal axis represents time, while the vertical axis represents the number of photons per unit (Count Per Second: CPS). The background light signals 45 were obtained for 100 seconds before a chemiluminescence reagent was dispensed, and then the chemiluminescence reagent was dispensed, and after the dispensation, ATP chemiluminescent signals 46 were obtained for 250 seconds. After the chemiluminescence reagent was dispensed, a flash type (highly sensitive type chemiluminescence reagent is immediately added which shows a peak value 48 of the signal intensity in a few seconds.

Figure 7B:
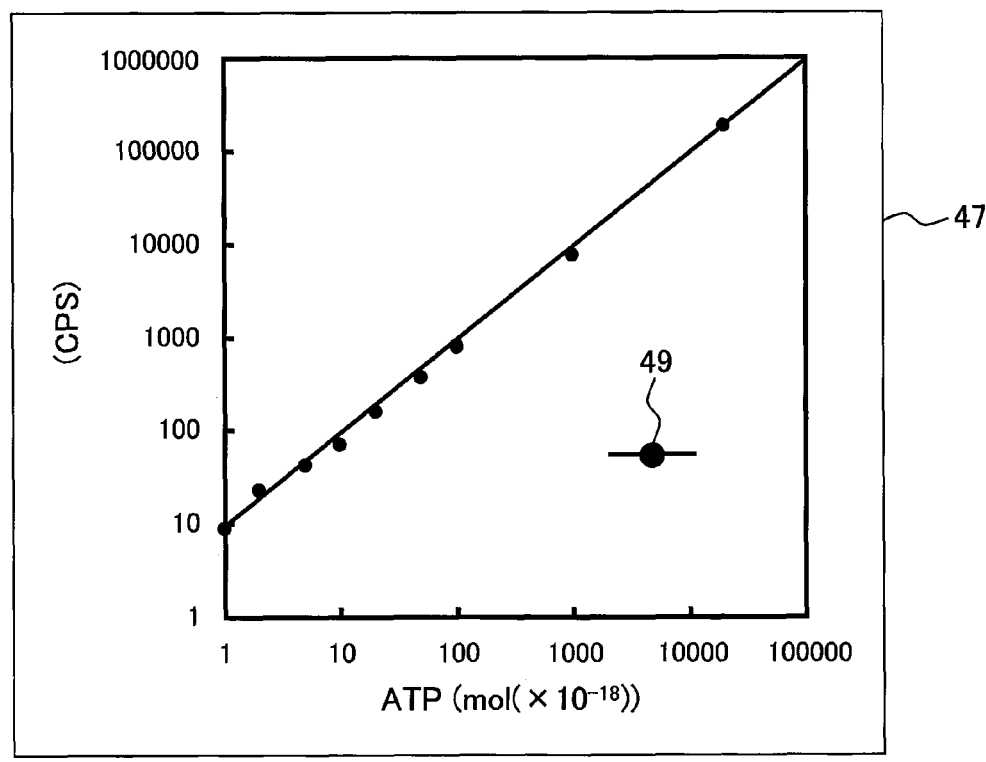
FIG. 7B is a graph showing a relationship between ATP concentration and luminescence intensity which is obtained using an apparatus for chemiluminescent assay and detection having a dispenser according to the second embodiment.

FIG. 7B is a graph 47 showing a typical example of a chemiluminescence curve, in which the differences between the peak values and the values of background light signals 44 of FIG. 7A are converted into numerical values and plotted relative to each concentration. The calibration curve 49 is linear within a range from a very low concentration of 1 amol to 100000 amol, which indicates a quantitative change of intensity. This result is obtained because the apparatus for chemiluminescent assay and detection of the present embodiment is highly sensitive and quantitative. In the present embodiment, any influence of entrance of stray light onto the background light signals 45 when the sample container 4 is exchanged is eliminated by the plate member 9 of the second light shielding BOX 6, and also the photodetector gets closer to the container for measurement to achieve a large solid angle. Therefore, the calibration curve 47 of FIG. 7B is an ideal calibration curve as a result obtained by measuring weak chemiluminescent signals with high sensitivity at a very low concentration.

Furthermore, the calibration curve graph 47 of FIG. 7B is important to count the number of a trace amount of microbes, on the order of the several number of microbes for example. This is the indispensable data for an experimental system for monitoring the number of airborne microorganisms in a clean room using the microbe count function according to a third embodiment which will be explained below.

Meanwhile, when an ATP measurement at a high concentration is required to examine a high water contamination level and the like, the calibration curve of FIG. 7B cannot be used to evaluate the contamination level. However, in the apparatus for chemiluminescent assay and detection of the present embodiment, since the distance between the photodetector 13 and the bottom of the sample container 4 can be controlled as needed, any calibration curve can be constructed depending on a required concentration range. Specifically, when the upper limit of a dynamic range is too low for a sample to be detected which has an extremely high luminescence intensity, the distance between the photodetector 13 and the bottom of the sample container 4 can be correspondingly increased. For example, when the second actuator 12 which is electrically driven is used, since the moving distance is determined by the number of pulses sent to the motor, a distance proper to each of detectable sensitivity ranges is found in advance by conducting an experiment, and the number of pulses at the experiment is stored in a storing medium of a controller. As need arises, a proper number of pulses is selected to quickly change the distance to the container. When the second actuator 12 which is driven by air is used, a stopper is provided to physically control the distance. That is, a position of the stopper depending on sensitivity is found by conducting an experiment in advance, which enables the distance control.

<Third Embodiment>

A third embodiment relates to an apparatus for chemiluminescent assay and detection having a microbe count function for counting the number of living microbes. The apparatus selectively detects only ATP which is contained in the living microbes, and measures the amount of the ATP. The ATP content of each type of microbes is already known, thereby the number of microbes can be calculated based on the calibration curve of FIG. 7B according to the second embodiment. For example, the ATP content of one *Escherichia coli* is 2 amol to 3 amol.

Figure 8A:
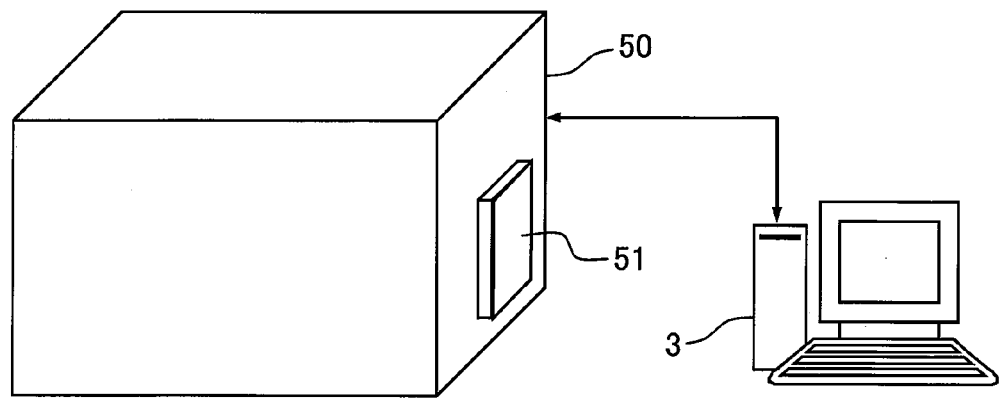
FIG. 8A is a view showing the outline of a chemiluminescence apparatus having a function for counting microbes according to a third embodiment.
Figure 8B:
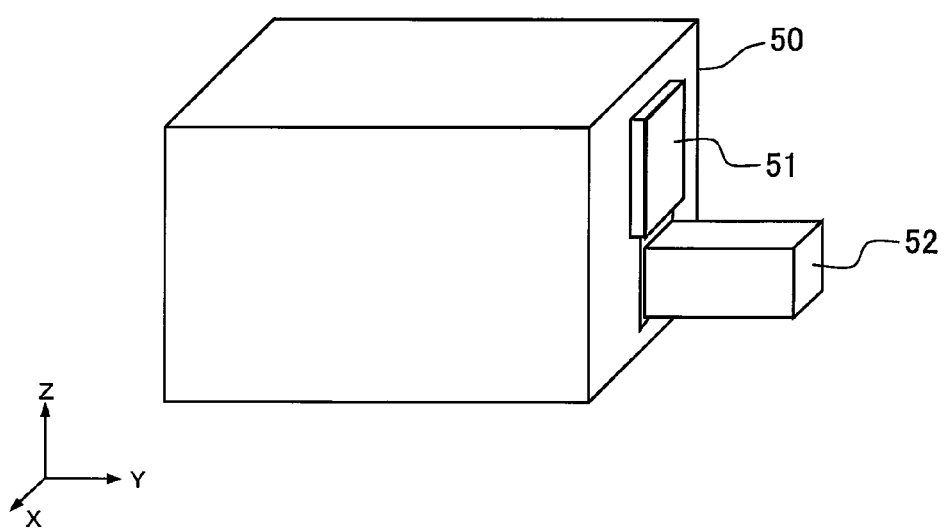
FIG. 8B is a view showing a chemiluminescence apparatus having a function for counting microbes according to the third embodiment with a light-shielding stage being drawn outside.
Figure 9:
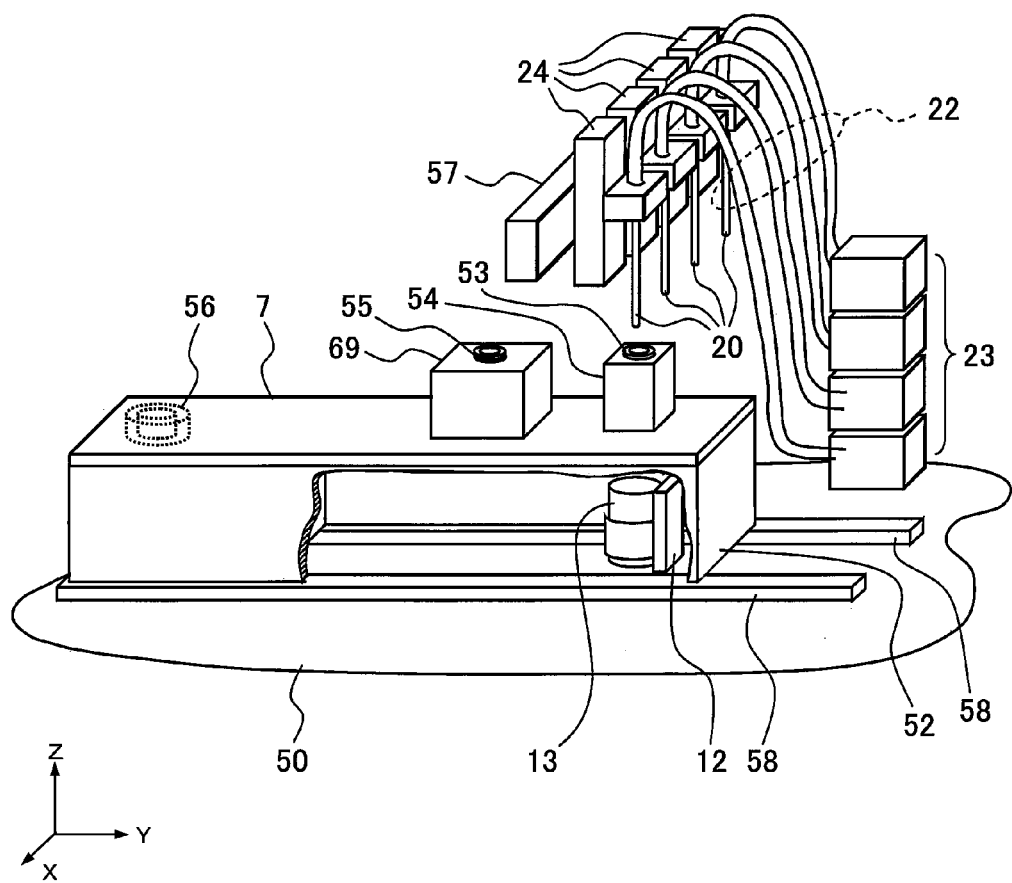
FIG. 9 is a view showing a schematic structure of a chemiluminescence apparatus having a function for counting microbes according to the third embodiment.

FIGS. 8A and 8B and FIG. 9 are views showing the outline of a system including an apparatus for chemiluminescent assay and detection 50 having a microbe count function according to the third embodiment and the control device 3. The apparatus for chemiluminescent assay and detection 50 having a microbe count function is automatically controlled by the control device 3. The command from the control device 3 causes the openable/closable window 51 to be in an open state, so that a light-shielding stage 52 is moved outside of the apparatus, on which a sample preparation container 53 and a chemiluminescence detection container 55 are placed (FIGS. 8A and 8B). Single-purpose containers 53 and 55 are mounted to a sample preparation container holder 54 and a chemiluminescence detection container holder 69 respectively.

With reference to FIG. 9, the structure of the apparatus for chemiluminescent assay and detection 50 having a microbe count function will be explained below. The apparatus for chemiluminescent assay and detection 50 includes three dispensers and one fluid dispenser, and two of the dispensers is means for dispensing a reagent to the sample preparation container 53, and the other one of the dispensers is means for dispensing a chemiluminescence reagent to the chemiluminescence detection container 55. The fluid dispenser is means for collecting the solution after preparation in the sample preparation container 53 and dispensing the collected solution into the chemiluminescence detection container 55. In the present embodiment, the reagent to be dispensed other than a chemiluminescence reagent is an ATP eliminating reagent and an ATP extracting reagent. The dispensing nozzles 20 are provided with a group of third actuators 24 for the movement in the direction of the z-axis and a fifth actuator 57 for the movement in the direction of x-axis, which allows the dispensing nozzles 20 to be inserted in the sample preparation container 53, and controls the positions of the dispensing nozzles both in the x-axis and the z-axis. The fifth actuator 57 is, for example, mounted to a gate-shaped plate member which is attached to the wall of the first light shielding BOX 6, similar to the second actuator 24 of the first embodiment.

Figure 11:
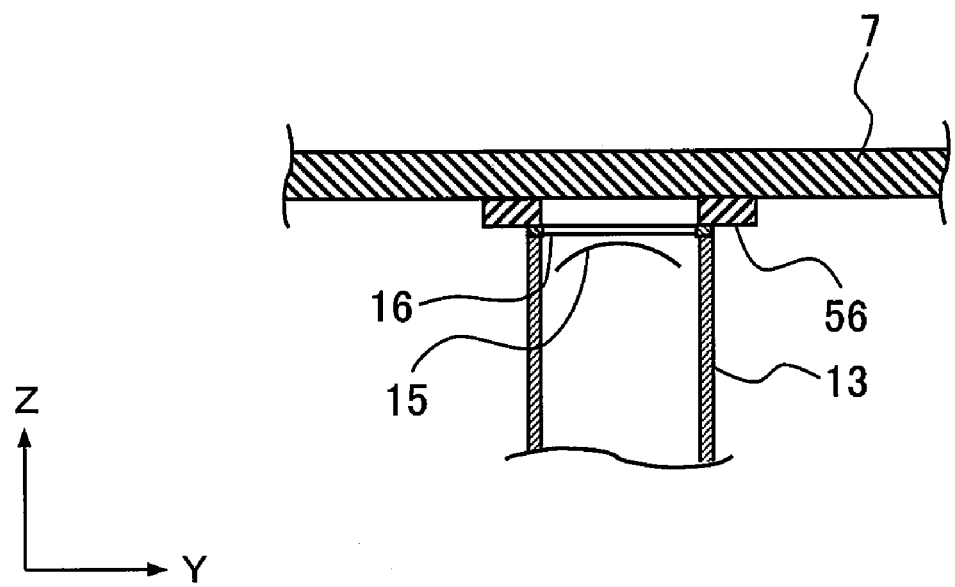
FIG. 11 is a view showing a state in which a sensitive area of a photodetector is shielded using a light shielding attachment based on the operation principle of a chemiluminescence apparatus having a function for counting microbes according to the third embodiment.

The light-shielding stage 52 includes the photodetector 13 therein with the photodetector 13 being mounted to the second actuator 12. The light-shielding stage 52 is movable in the direction of the y-axis by a fourth actuator 58. The light-shielding stage 52 has a top plate having a through hole formed therein, over which the chemiluminescence detection container holder 69 is placed. The apparatus for chemiluminescent assay and detection 50 further includes a tubular light shielding attachment 56. The light shielding attachment 56 enables a light shielding, as shown in FIG. 11, when the PMT moves in the direction of the z-axis so that the tip portion of the photodetector 13 is compressed against and sealed by the light shielding attachment 56. Since the light shielding attachment 56 is made of a resilient material, a pressing of the photodetector 13 in the direction of the z-axis against the light shielding attachment 56 enables blocking of stray light. As the resilient material, for example, a black viton rubber/or fluorine contained rubber which is used to make O-rings for leak prevention of vacuum apparatuses is preferable. That is, in the state shown in FIG. 8B, the through hole of the light-shielding stage 52 is not covered with the sample preparation container holder 54 or the chemiluminescence detection container holder 69, the protection of a sensitive area of the photodetector 13 is needed. Thus, in the state shown in FIG. 8B, the tip portion of the photodetector 13 is pressed against the light shielding attachment 56, so that the sensitive area of the photodetector 13 is protected from stray light.

Figure 10:
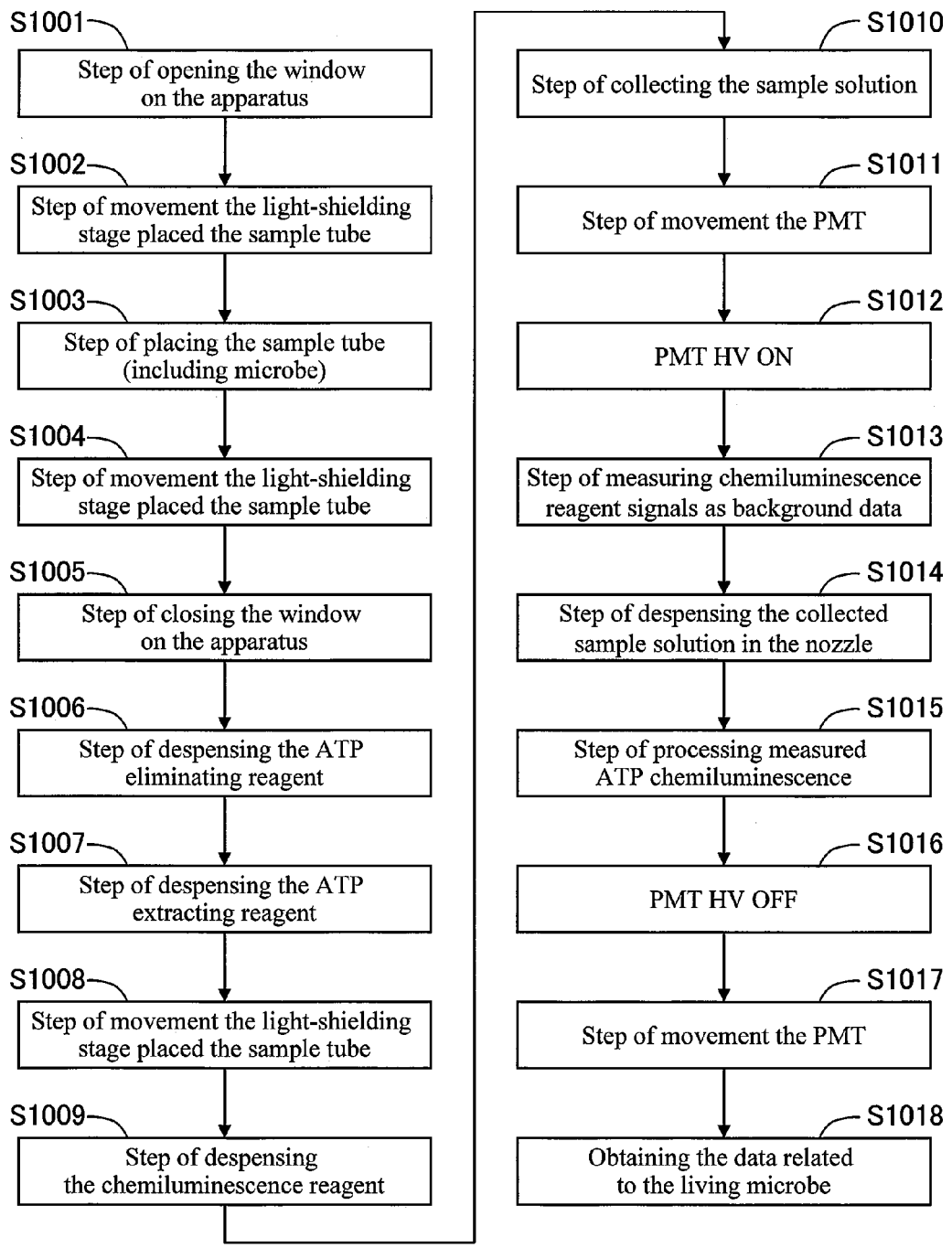
FIG. 10 is a flowchart illustrating a procedure for measuring the amount of ATP in living microbes using a chemiluminescence apparatus having a function for counting microbes according to the third embodiment.

Next, with reference to FIG. 10, a procedure for counting living microbes using the apparatus shown in FIG. 9 will be explained below. First, an openable/closable window 51 is opened (S1001), and the light-shielding stage moves (S1002). At this step, the sample preparation container 53 and the chemiluminescence detection container 55 in which a cell suspension containing collected microbes therein are stored are placed (S1003). After the placement, the light-shielding stage is moved into the microbe count apparatus 50 (S1004). Then, the openable/closable window 51 is closed (S1005).

Next, an ATP eliminating reagent is dispensed in the sample preparation container 53 to eliminate the exogenous ATP except living microbe and the ATP from killed microbe (S1006). After the reaction is completed, an ATP extracting reagent is dispensed in the sample preparation container 53 (S1007), and the light-shielding stage 52 is moved to a position which allows a dispensation from the chemiluminescence detection container 55 (S1008). Next, a chemiluminescence reagent is dispensed in the chemiluminescence detection container 55 (S1009). However, the dispensation of the chemiluminescence reagent may be conducted before/after the injection of the ATP eliminating reagent.

The sample solution which is already prepared to be dispensed in the chemiluminescence detection container 55 is collected from the sample preparation container 53 before the measurement is started (S1010). The amount of the collected solution should be adjustable within a range from several microliters to several milliliters, and the system of the feed pump 23 preferably uses a combination of a syringe and a syringe pump. In the above steps, the state shown in FIG. 11 is a characteristic which constrains light accumulation due to stray light when a container is placed.

Then, the photodetector 13 moves in the direction of the z-axis (S1011) to be inserted in the through hole of the top plate, and an HV is applied to PMT which is the photodetector 13 (S1012). After background light signals are measured from under the bottom of the chemiluminescence detection container to which the chemiluminescence reagent was dispensed (S1013), the collected sample solution after preparation is dispensed in the chemiluminescence detection container 55 (S1014). The ATP contained in the prepared sample solution reacts with the chemiluminescence reagent and emits chemiluminescence. The ATP chemiluminescence is measured (S1015). Then the HV applied to PMT is turned off (S1016), and the second actuator 12 is driven to cause the tip portion of the photodetector 13 to move in the direction of the z-axis to a position below the top plate 7 of the light-shielding stage 52, and also move in the direction of the y-axis, so that the tip portion of the photodetector 13 is compressed and sealed by the light shielding attachment 56 (S1017).

The resulting ATP luminescence intensity and the calibration curve of FIG. 7B according to the second embodiment are used to calculate the number of microbes, and the data is sent (S1018). In other words, the number of microbes can be calculated based on the known ATP amount of each microbe. For example, bacillus subtilis contains 17 amol/cell, *staphylococcus aureus* contains 1.52 amol/cell, and *Escherichia coli* contains 3 amol/cell.

In the present embodiment, a chemiluminescence measuring apparatus having a microbe count function for counting the number of living microbes which uses the biology chemiluminescence reaction of ATP, but the applicable scope of an automation equipment which includes an automatic specimen preparation mechanism for automatic sample preparation and a chemiluminescence detection mechanism with high sensitivity is not limited to the microbe count function. As a modified example of the present embodiment, for example, a system for automatically measuring an amount of chemiluminescence can be achieved in which a specimen solution containing an antigen of a concentration which is not known is used as a specimen, and a chemiluminescence reagent containing an excess amount of luciferin and ATP is used as a chemiluminescence reagent, and a sample preparation mechanism is used, so that an antigen-antibody reaction in so-called sandwich immunoassay technique is initiated with respect to the specimen antigen to produce a reaction solution which contains a luciferase labeled products of the amount which is proportional to the amount of the antigen, and then the reaction mixture is dispensed through a fluid dispensing mechanism into the chemiluminescence detection container 55 which stores a chemiluminescence reagent therein. The amount of chemiluminescence in the modified example is proportional to the amount of luciferase in the reaction mixture, that is the amount of an antigen-antibody reaction. Therefore, an immunoassay system with high sensitivity for measuring the amount of antigen by comparing with the amount of chemiluminescence of a standard antigen specimen having a known concentration can be achieved. The system can be applied to an apparatus for assay and detection of DNA and RNA with high sensitivity in which nucleic acid hybridization is used as a selective combination principle and luciferase is a label.

<Summary of Embodiments>

The first embodiment provides a chemiluminescence measuring apparatus of double light shielding type which includes a first light shielding BOX having an open/close door that is used to place or remove a sample container from a sample container holder, and a second light shielding BOX in the first light shielding BOX, the second light shielding BOX having a top plate which is partly configured as a shutter unit and has an openable/closable mechanism to see the first light shielding BOX therethrough, and has a photodetector housed therein. This completely blocks stray light to carry out a measurement of chemiluminescence at a high sensitivity and accuracy.

As to the specific structure for light shielding, basically, the top plate of the second light shielding BOX has at least one through hole formed therein for opening and closing, and a container holder in which a sample container is placed is placed over the through hole, and the shutter functions to open and close the through hole. A photodetector is placed on the bottom via an electrically operated actuator, so that when the shutter of the top plate of the second light shielding BOX is opened, a sensitive area of the photodetector in the second light shielding BOX is positioned opposite to the bottom of the sample container which is placed in the sample container holder.

When the first light shielding BOX is opened to place the container which stores a chemiluminescent material therein, the shutter of the top plate of the second light shielding BOX is closed. This blocks the entrance of stray light to the photodetector which may cause a variation in dark current values.

After the container which stores a chemiluminescent material therein is placed, the first light shielding BOX is closed. When a measurement is started, the shutter at the top plate of the second light shielding BOX is opened, and a sensitive area of the photodetector is inserted into the through hole by the electrically driven actuator. The electrically driven actuator can control the distance between the bottom of the sample container and the sensitive area of the photodetector as needed. The sensitive area of the photodetector may be positioned above the position of the shutter for double light shielding, which achieves a close arrangement to the bottom of the sample container. In this state, in order to measure chemiluminescence, the chemiluminescence can be efficiently collected to the sensitive area, and a so-called large solid angle can be formed, thereby chemiluminescence can be detected with high sensitivity and accuracy.

The second Embodiment is provided with means (such as a nozzle, a feed pump, and a liquid supply pipe) for dispensing a solution to a sample container in addition to the structure of the first embodiment.

Furthermore, the third embodiment provides an apparatus for chemiluminescent assay and detection with a microbe count function. The microbe count function can be achieved by providing a group of nozzles for collecting/dispensing a treatment solution for a reaction which is required to measure the amount of ATP from living microbes, solution supply pipes which are connected to the nozzles, a solution storing container for storing the treatment solution, and a pump which is the means for collecting/dispensing the solution through the tips of the nozzles, in the first light shielding BOX of the above described apparatus for chemiluminescent assay and detection of double light shielding type. The container holder for holding a container for measuring chemiluminescence is placed over the through hole formed in the top plate on the second light shielding BOX, and at least one another container holder which can have a container placed therein is placed at another position. Hereinafter, the latter container which is used to prepare a sample is referred to as a sample preparation container.

An ATP eliminating reagent is dispensed from the nozzle into the cell suspension in the specimen preparation container to eliminate killed microbes and floating ATP other than living microbes. Next, an ATP extracting reagent is dispensed to extract ATP of living microbes. In the above process, the photodetector is shielded from light by the second light shielding BOX. Next, a chemiluminescence reagent is dispensed in the container for measuring chemiluminescence, and finally a treated cell suspension is collected to be dispensed and mixed in the chemiluminescence reagent. Upon the mixture, or just before the mixture, a sensitive area of the photodetector is moved to a position above the top plate (the through hole is formed therein) of the second light shielding BOX so that the photodetector starts a measurement at a position closer to the container for measuring chemiluminescence. Since background light data can be obtained at the time of or before the dispensation, when a so-called flash type chemiluminescence reagent is used, the signal of the highest chemiluminescence just after the reaction is started can be obtained.

It is possible to add the structure of the third embodiment to that of the first or second embodiment. For example, the light shielding attachment 56 (see FIG. 11) may be added to the structure of the first or second embodiment. This guarantees a better light shielding property.

What is claimed is:

1. A luminescence assay and detection method, comprising:
    setting a container in a holder, the container storing a sample that is subject to luminescence assay and detection;
    after setting the container, moving a light shielding plate, which is so provided as to face a photodetector adapted to detect light, from a position facing the photodetector;
    after moving the light shielding plate, positioning a light receiving surface of the photodetector in such a manner as to face the container and at either the same position as a position of a surface of the light shielding plate facing the photodetector before the light shielding plate is moved or a position closer to the container than the position of the surface of the light shielding plate facing the photodetector before the light shielding plate is moved; and
    after the light receiving surface of the photodetector is positioned, performing luminescence assay and detection with respect to the sample by the photodetector.

2. The luminescence assay and detection method according to claim 1, further comprising prior to setting the container:
    providing the photodetector in a light shielding chamber having a through-hole in its top plate; and
    providing the light shield plate in such a manner as to close the through-hole.

3. The luminescence assay and detection method according to claim 2, further comprising, in positioning the light receiving surface of the photodetector, moving the light receiving surface of the photodetector in such a manner that at least a tip part of the photodetector passes the through-hole.

4. The luminescence assay and detection method according to claim 2, further comprising positioning the holder above the through-hole before setting the container.

5. The luminescence assay and detection method according to claim 2, further comprising, in positioning the light receiving surface of the photodetector:
    pre-setting the container in such a manner that at least a bottom part of the container is located in an internal space of the holder that leads to the through-hole; and
    after the through-hole has been passed, moving at least a tip part of the photodetector into the internal space so that it is positioned facing the container within the internal space.

6. The luminescence assay and detection method according to claim 1, further comprising, in positioning the light receiving surface of the photodetector, moving the photodetector relative to the light shielding plate in such a manner that the direction in which the light shielding plate is moved is perpendicular to the direction in which the photodetector is moved.

7. The luminescence assay and detection method according to claim 1, further comprising, in performing the luminescence assay and detection, controlling a distance between a bottom portion of the container and the photodetector facing the container in accordance with a signal intensity of the light.

8. The luminescence assay and detection method according to claim 1, further comprising dispensing a chemiluminescence reagent into the container after moving the photodetector.

* * * * *